(12) United States Patent
Van Dyk (10) Patent No.: US 7,384,788 B2
(45) Date of Patent: Jun. 10, 2008

(54) REGULATOR/PROMOTER FOR TUNABLE GENE EXPRESSION AND METABOLITE SENSING

(75) Inventor: Tina K. Van Dyk, Wilmington, DE (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 317 days.

(21) Appl. No.: 11/165,160

(22) Filed: Jun. 23, 2005

(65) Prior Publication Data
US 2005/0266569 A1 Dec. 1, 2005

Related U.S. Application Data

(62) Division of application No. 10/759,889, filed on Jan. 16, 2004, now Pat. No. 6,943,028.

(60) Provisional application No. 60/440,965, filed on Jan. 17, 2003.

(51) Int. Cl.
 C12N 15/74 (2006.01)
 C12N 1/20 (2006.01)
 C12N 15/63 (2006.01)
(52) U.S. Cl. .................................... 435/471; 435/252.1
(58) Field of Classification Search ..................... None
 See application file for complete search history.

(56) References Cited

U.S. PATENT DOCUMENTS 5,292,643 A 3/1994 Shibano et al.

FOREIGN PATENT DOCUMENTS

WO WO 89/09823 A1 10/1989

OTHER PUBLICATIONS

Everett et al. Pendred syndrome is caused by mutations on a putative sulphate transporter gene (PDS). Nature Genetics 17: 411-422. 1997.*
Scott et al. The Pendred syndrome gene encodes a chloride-iodide transport protein. Nature Genetics 21: 440-443. 1999.*
Watson et al. Predicting protein function from sequence and structural data. Current Opinion in Structural Biology 15:275-284. 2005.*
U.S. Appl. No. 60/440,760, Sariaslani et al.
Donovan et al., Review: Optimizing inducer and culture conditions for expression of foreign proteins under the control of the IAC promoter, J. Ind. Microbiol. 16:pp. 145-154, 1996.
Schell, Molecular Biology of the LysR Family of Transcriptional Regulators, Annu. Rev. Microbiol. 47: 597-626, 1993.
Sperandio et al., Quorum-Sensing *Escherichia coli* Regulator A: a Regulator of the LysR Family Involved In the Regulation of the Locus of Enterocyte Effacement Pathogenicity, Island in Enterohemorrhagic *E. coli.*, Infect. Immun, 70: pp. 3085-3093, 2002.
Serebriiskii and Golemis, Uses of lacZ to Study Gene Function: Evaluation of β-Galactosidase Assays Employed in the Yeast Two-Hybrid System, Anal. Biochem. 285: p. 1-15, 2000.
Spergel et al., Using reporter genes to label selected neuronal populations in transgenic mice for gene promoter, anatomical, and physiological studies, Prog. Neurobiol. 63: pp. 673-686, 2001.
Yarranton, Inducible vectors for expression in mammalian cells, Curr. Opin. Biotechnol. 3:pp. 506-511, 1992.
Van Dyk et al., A genomic approach to gene fusion technology, Proc. Nat. Acad. Sci. USA 98: 2555-2560, 2001.
VanDyk et al., LuxArray, a High-Density, Genomewide Transcription Analysis of *Escherichia coli* Using Bioluminescent Reporter Strains, J. Bacteriol. 183: pp. 5496-5505, 2001.
Diaz et al., Biodegradation of Aromatic Compounds by *Escherichia coli*, Microbiol. Mol. Biol. Rev. 65: pp. 523-569, 2001.
Bundy et al.,Synergistic transcriptional activation by one regulatory protein in response to two metabolites, Proc. Natl. Acad. Sci. USA 99: pp. 7693-7698, 2002.
Paulsen et al., A family of Gram-negative bacterial outer membrane factors that function in the export of proteins, carbohydrates, drugs and heavy metals from Gram-negative bacteria, FEMS Microbiol. Lett. 156: pp. 1-8, 1997.
Database EMBL Online, Dec. 30, 1994, *Escherichia coli* K-12 chromosomal region from 67.4 to 76.0 minutes, Accession No. U18997.
Database EMBL Online, Nov. 1, 1995, Putative HtH-type transcriptional regulator yhcS, Accession No. P45691.

* cited by examiner

*Primary Examiner*—David Guzo
*Assistant Examiner*—Michele K Joike (57) ABSTRACT

A method for the facile and inexpensive inducible expression of heterologous genes has been discovered. The yhcS regulator gene has been found to be inducible by aromatic carboxylic acids and to alter the expression of operons in the LysR gene family, including the yhcRQP operon, common in enteric bacteria. Heterologous nucleic acid molecules placed under the control of yhcS responsive promoters may be overexpressed in response to the presence of inexpensive aromatic carboxylic acids.

6 Claims, 1 Drawing Sheet

FIG. 1

REGULATOR/PROMOTER FOR TUNABLE GENE EXPRESSION AND METABOLITE SENSING

This application claims the benefit of United States Provisional Application 60/440,965 filed Jan. 17, 2003, which is hereby incorporated in its entirety by reference.

FIELD OF INVENTION

The present invention relates to the fields of molecular biology and microbiology. More specifically, this invention pertains to a novel system for controlling gene expression levels that is induced by inexpensive, environmentally friendly, small molecules.

BACKGROUND

There is a need in the field of microbial metabolic engineering for tunable promoters and novel regulatory switches for the inducible expression of heterologous proteins. The "old standard" lac promoter/Lac repressor system is still widely used. However, the commonly used inducer, isopropylthio-beta-D-galactoside ("IPTG"), is expensive and thus not practical for large-scale bioprocesses. Additionally, higher concentrations of IPTG increase the metabolic burden on the cell, in turn reducing the maximal expression of the target gene (Donovan et al., *J. Ind. Microbiol.* 16:145-154 (1996)). The few available alternatives also have limitations.

One possible solution to this problem is to appropriate existing genetic systems of transcriptional regulators to enhance heterologous gene expression. A number a of transcriptional regulators are known. For example, the LysR family of transcriptional regulators is one of the largest groups of transcriptional regulators in prokaryotes (Schell, *Annu. Rev. Microbiol.* 47:597-626 (1993)). Currently, there are over 80 known members of this regulator family. Proteins having greater than 20% amino acid identity with another LysR family member or having the consensus sequence of the N-terminal region of the LysR family are considered to be members of this regulator family. LysR family members are also commonly found in the size range of 276 to 324 amino acids, bind to similar DNA sequences in the absence of inducers, have promoters that are located close to or overlapping those of the regulated target gene, and most can repress their own transcriptional levels 3- to 10-fold. Activation of the regulated target gene occurs in the presence of inducer and usually results in a 6- to 200-fold increase in regulated target gene transcription. Regulated target genes are diverse and have numerous functions.

Recently, the gene encoded by open reading frame ("ORF") b3243 in *Escherichia coli* ("*E. coli*") has been demonstrated to function via quorum sensing (Sperandio et al., *Infect. Immun.* 70:3085-3093 (2002)). Quorum sensing is the ability of bacteria cells to communicate with one another through perception of the accumulation of signaling molecules based on bacteria cell density. The gene encoded by ORF b3243 is up-regulated via quorum sensing resulting in a 23-fold increase in transcription of the gene. The protein produced by the b3243 ORF was not purified. The gene was found to have a role in the regulation of the LEE genes involved in a type III secretion system, a pathogenecity system that serves to translocate, upon contact with eukaryotic host cells, proteins from the bacteria cytoplasm into the host cell cytoplasm. As the b3243 ORF gene is a putative regulator of the LysR family, the b3243 ORF gene itself was able to induce a four-fold induction of LEE1 transcription. No inducer of the b3243 ORF gene was identified. One in the art will appreciate that this inefficient induction prevents the b3243 ORF gene from being a viable promoter/regulator system without the identification of its inducer.

The use of promoter/reporter gene constructs is well known in the art (Serebriiskii and Golemis, *Anal. Biochem.* 285:1-15 (2000); Spergel et al., *Prog. Neurobiol.* 63:673-686 (2001); Yarranton, *Curr. Opin. Biotechnol.* 3:506-511 (1992)). Particularly, reporter systems utilizing β-galactosidase, green florescent protein, luciferase, and chloramphenicol acetyl transferase (CAT) are all commonly used in the art. Additionally, reporter systems such as luxCDABE are useful because this operon contains all of the genes required for bioluminescent reporting ((Van Dyk et al., *Proc. Nat. Acad. Sci. USA* 98:2555-2560 (2001)).

The luxCDABE operon has been utilized to create a collection of random gene fusions, comprising 27% of the known or predicted transcriptional units of *E. coli* (Van Dyk et al., *J. Bacteriol.* 183:5496-5505 (2001)). Treatment of *E. coli* cells containing these gene fusions with nalidixic acid, a quinolone, results in selective up-regulation of ten genes. Some of these up-regulated genes are LexA-regulated SOS genes, while others are not generally induced by DNA damage.

Aromatic compounds such as aromatic carboxylic acids are usually toxic to microorganisms. Numerous bacterial strains resistant to aromatic compounds, however, are known in the prior art (Diaz et al., *Microbiol. Mol. Biol. Rev.* 65:523-569 (2001)). Additionally, a LysR family member from *Acinetobacter*, BenM, is responsive to synergistic induction by benzoic acid, an aromatic carboxylic acid, and muconic acid (Bundy et al., *Proc. Natl. Acad. Sci. USA* 99:7693-7698 (2002)). Benzoic acid alone, however, produces minimal, if any, induction of BenM activity. Even the synergistic response with muconic acid produces only a four-fold increase in BenM activity.

U.S. Pat. No. 5,292,643 issued to Shibano et al. on Mar. 8, 1994 describes genes related to fusaric acid resistance in variety of microorganisms. Specifically, genes capable of decomposing or detoxifying fusaric acid are disclosed. One of the genes postulated to be involved in fusaric acid resistance, fusB, shares some homology with the putativTe efflux transporter (PET) yhcP gene (Paulsen et al., *FEMS Microbiol. Lett.* 156:1-8 (1997)). Applicants incorporate by reference the co-owned and concurrently filed application entitled "PET Family of Efflux Proteins", U.S. Patent Application No. 60/440,760, which describes new proteins efflux proteins whose expression may alter the expression of carboxylic acids.

The problem to be solved therefore is to discover facile and inexpensive methods of inducible expression of heterologous genes. Applicants have solved the stated problem through the discovery that the promoter elements of the yhcRQP operon are responsive to the expression of the yhcS regulator (a member of the LysR family of transcriptional regulators) whose expression may be induced by an inexpensive cadre of aromatic carboxylic acid inducers.

SUMMARY OF THE INVENTION

The invention relates to the discovery that the yhcS regulator is responsible for the activation of the yhcRQP operon promoter and is inducible by aromatic carboxylic acids, compounds that are typically toxic to cells. The expression of heterologous genes, placed under the control of a yhcRQP operon promoter may be regulated by the presence of an aromatic carboxylic acid. Accordingly the invention provides a method for the inducible expression of a heterologous nucleic acid molecule comprising:

a) providing a host cell having a genome comprising:
   i) a yhcS regulator gene responsive to an aromatic carboxylic acid inducer;
   ii) a promoter region, responsive to expression of the yhcS regulator gene; and
   iii) at least one heterologous nucleic acid molecule; wherein the at least one heterologous nucleic acid molecule is operably linked to the promoter region;
b) contacting the host cell of (a) with an aromatic carboxylic acid inducer wherein the at least one heterologous nucleic acid molecule is expressed.

In a preferred embodiment the invention provides a method for the inducible expression of a heterologous nucleic acid molecule comprising:

a) providing an enteric bacterial host cell having a genome comprising:
   i) a yhcS regulator gene responsive to an aromatic carboxylic acid inducer;
   ii) a promoter region, responsive to expression of the yhcS regulator gene; and
   iii) at least one heterologous nucleic acid molecule; wherein the at least one heterologous nucleic acid molecule is operably linked to the promoter region;
b) contacting the host cell of (a) with an aromatic carboxylic acid inducer wherein the at least one heterologous nucleic acid molecule is expressed.

Specific yhcS regulator gene useful in the present invention are those that are selected from the group consisting of:

a) an isolated nucleic acid molecule comprising nucleic acid sequence SEQ ID NO:1; and
b) an isolated nucleic acid molecule, which hybridizes to SEQ ID NO:1 after being washed with 0.1×SSC, 0.1% SDS at 65° C. and washed with 2×SSC, 0.1% SDS followed by a second wash in 0.2×SSC, 0.1% SDS.

Similarly specific promoter responsive to expression of the yhcS regulator gene are those selected from the group consisting of:

a) an isolated nucleic acid molecule comprising nucleic acid sequence SEQ ID NO:3; and
b) an isolated nucleic acid molecule, which hybridizes to SEQ ID NO:3 after being washed with 0.1×SSC, 0.1% SDS at 65° C. and washed with 2×SSC, 0.1% SDS followed by a second wash in 0.2×SSC, 0.1% SDS.

In another embodiment the invention provides a host cell comprising:

a) a yhcS regulator gene responsive to an aromatic carboxylic acid inducer having a nucleic acid sequence selected from the group consisting of:
   i) an isolated nucleic acid molecule comprising nucleic acid sequence SEQ ID NO:1; and
   ii) an isolated nucleic acid molecule, which hybridizes to SEQ ID NO:1 after being washed with 0.1×SSC, 0.1% SDS at 65° C. and washed with 2×SSC, 0.1% SDS followed by a second wash in 0.2×SSC, 0.1% SDS;
b) a promoter region, responsive to expression of the yhcS regulator gene having a nucleic acid sequence selected from the group consisting of:
   i) an isolated nucleic acid molecule comprising nucleic acid sequence SEQ ID NO:3; and
   ii) an isolated nucleic acid molecule, which hybridizes to SEQ ID NO:3 after being washed with 0.1×SSC, 0.1% SDS at 65° C. and washed with 2×SSC, 0.1% SDS followed by a second wash in 0.2×SSC, 0.1% SDS; and
iii) at least one heterologous nucleic acid molecule; wherein the at least one heterologous nucleic acid molecule is operably linked to the promoter region.

BRIEF DESCRIPTION OF THE DRAWINGS AND SEQUENCE DESCRIPTIONS

The invention can be more fully understood from the following detailed description, figures and the accompanying sequence descriptions, which form a part of this application.

The following sequences conform with 37 C.F.R. 1.821-1.825 ("Requirements for patent applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the yhcS regulator.

SEQ ID NO:2 is the amino acid sequence of the YhcS protein.

SEQ ID NO:3 is the nucleotide sequence of the promoter region upstream of yhcQ.

SEQ ID NO:4 is the nucleotide sequence of the primer Kan-2FP(PCR).

SEQ ID NO:5 is the nucleotide sequence of the primer Kan-2RP(PCR).

SEQ ID NO:6 is the nucleotide sequence of the primer Kan-2FP-1.

SEQ ID NO:7 is the nucleotide sequence of the primer Kan-2RP-1.

SEQ ID NO:8 is the nucleotide sequence of the primer YhcS.F.

SEQ ID NO:9 is the nucleotide sequence of the primer YhcS.R.

DETAILED DESCRIPTION OF THE INVENTION

There is a need in the field of microbial metabolic engineering for tunable promoters and novel regulatory switches. Advantages of Applicants' system are the very low basal levels of gene expression in the absence of inducer and expression levels that vary with the concentration of inducer up to relatively high expression levels. Furthermore, the cost of many of the inducing molecules is relatively inexpensive.

There are numerous uses for Applicants' tunable promoter system comprising the YhcS regulatory protein and the responsive promoter region. This novel promoter/regulator system can be used to control and regulate expression of genes and operons of interest by applying standard molecular biology methods as has been demonstrated herein by the controlled expression of luxCDABE.

Another possible application is suggested by analogy to other LysR family proteins, which typically have a conformational change upon binding their cognate inducer. YhcS protein likely binds to certain aromatic carboxylic acid molecules and changes conformation such that it activates gene expression upon DNA binding. This conformation change may be useful to sense small molecules in applications such as those found in nano scale systems.

The range of molecules to which YhcS responds may be manipulated by application of a variety of protein engineering techniques. Thus, the useful range of molecules of each of the above-mentioned applications could be expanded.

Advantages of this regulator/promoter system include, but are not limited to, basal expression levels that are extremely low; high levels of expression following induction; inexpensive, environmentally friendly inducers; when used in conjunction with other expression systems, an alternative expression system that will allow differential regulation of various genes in a genetically engineered host; and a protein conformation change useful for nanotechnology.

Applicants specifically incorporate the entire content of all cited references in this disclosure.

In the context of this disclosure, a number of terms shall be utilized.

The term "pHBA" is the abbreviation for para-hydroxybenzoic acid, which is also known as para-hydroxybenzoate.

The term "PHCA" is the abbreviation for para-hydroxycinnamic acid, which is also known as para-hydroxycinnamate.

The term "CA" is the abbreviation for cinnamic acid, which is also known as cinnamate An "isolated nucleic acid molecule" refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), particularly Chapter 11 and Table 11.1 therein (entirely incorporated herein by reference) (hereinafter "Sambrook"). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by a second wash in 0.2×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook supra). For hybridizations with shorter nucleic acids, i.e., oligonucleotides, the position of mismatches becomes more important, and the length of the oligonucleotide determines its specificity (Sambrook supra). In one embodiment the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403-410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular bacterial proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data*, Part I (Griffin, A. M., and Griffin, H. G., eds.) Humana Press, New Jersey (1994); *Sequence Analysis in Molecular Biology* (von Heinje, G., ed.) Academic Press, New York (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387-395 (1984)), BLASTP, BLASTN, and FASTA (Pearson et al, *Proc. Natl. Acad. Sci. USA* 85:2444-2448 (1988). The BLASTX program is publicly available from NCBI and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403-410 (1990); Altschul et al., *Nucleic Acids Res.* 25:3389-3402 (1997)). Another preferred method to determine percent identity is by the method of DNASTAR protein alignment protocol using the Jotun-Hein algorithm (Hein et al., *Meth. Enzymol.* 183:626-645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy-terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences is the same then the two sequences are said to exhibit 50% homology.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Genome" refers to the entire genetic information contained within an organism (e.g., chromosome, plasmid, plastid, or mitochondrial DNA). "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. "Structural gene" refers to a gene that codes for the amino acid sequence of a protein or for a ribosomal RNA or transfer RNA. An "operon" refers to a controllable unit of transcription consisting of a number of structural genes transcribed together.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"Heterologous" as used in the context of gene expression relates to that which is "foreign" to a particular environment. Thus, a "heterologous gene" or "heterologous nucleic acid molecule" means a nucleic acid molecule that is foreign, or non-native to a particular host or genome. A "heterologous protein" is a protein that is foreign to a host cell and is typically encoded by a heterologous gene. Heterologous nucleic acids of the invention are typically expressed under the control of regulated promoters in an inducible fashion.

The term "regulator" refers to a protein whose primary function is to control the rate of expression of regulated genes. Regulation of gene expression can be by positive activation or by repression. A "regulatory gene" refers to a gene that encodes a regulator. Within the context of the present invention a typical regulator gene is the yhcS gene "Host cell" refers to a cell into which has been introduced (e.g., transformed or transfected) an exogenous polynucleotide sequence, i.e. a heterologogus nucleic acid molecule. Host cells are typically prokaryotic cells such as bacteria, e.g., *E. coli*, and may be eukaryotic cells such as yeast, insect, amphibian, green plant, or mammalian cells, where the relevant regulator genes exist.

"Inducer" refers to a small molecule that initiates transcription, or increases the rate of transcription, of a desired gene. Within the context of the present invention typical inducers are aromatic carboxylic acids having the ability to activate a regulator gene.

"Reporter gene" refers to a gene that encodes an easily assayed product (e.g. luxCDABE, bgaB, cat, dsRed, galK, gfp, lacZ, luc, luxAB, nptll, phoA, uidA, or xylE). Typically reporters are coupled to the promoter and/or regulator sequence of another gene and transfected into a host cell. The reporter gene can then be used to see which factors activate response elements in the upstream region of the gene of interest.

"Translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotechnol.* 3:225 (1995)).

"3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet and has an effect on cellular processes.

The term "operably linked" refers to the association of nucleic acid sequences on a single nucleic acid molecule so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

The term "expression" refers to the transcription and stable accumulation of sense (mRNA) or antisense RNA derived from the nucleic acid molecule of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or nontransformed organisms. "Co-suppression" refers to the production of sense RNA transcripts capable of suppressing the expression of identical or substantially similar foreign or endogenous genes (U.S. Pat. No. 5,231,020).

"Transformation" refers to the transfer of a nucleic acid molecule into the genome of a host organism, resulting in genetically stable inheritance. Host organisms containing the transformed nucleic acid fragments are referred to as "transgenic" organisms.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"PCR" or "polymerase chain reaction" is a technique used for the amplification of specific DNA segments (U.S. Pat. Nos. 4,683,195 and 4,800,159).

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Sambrook"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention relates to the discovery that aromatic carboxylic acids induce the up-regulation or expression of the regulator gene yhcS which in turn is responsible for the activation of the promoter region driving expression of the yhcRQP operon. Expression of heterologous nucleic acid molecules which are operably to these promoters may therefore be inducibly regulated by the presence or absence of inexpensive aromatic carboxylic acids in the medium.

Regulator Systems

The yhcS regulator and the corresponding yhcRQP operon is known and is common in a variety of enteric bacteria such as *Escherichia* (Hayashi et al., "Complete genome sequence of enterohemorrhagic *Escherichia coil* O157:H7 and genomic comparison with a laboratory strain K-12", *DNA Res.* 8 (1), 11-22 (2001)); *Yersinia* (Parkhill et al., "Genome sequence of *Yersinia pestis*, the causative agent of plague", *Nature* 413 (6855), 523-527 (2001)); *Shigella* (Wei et al., "Complete Genome Sequence and Comparative Genomics of *Shigella flexneri* Serotype 2a Strain 2457T", *Infect. Immun.* 71(5), 2775-2786 (2003)); and *Salmonella* (McClelland et al., "Complete genome sequence of *Salmonella enterica* serovar *Typhimurium* LT2"; *Nature* 413 (6858), 852-856 (2001)). It will be appreciated by one of skill in the art that those organisms having homologs to the present regulators will be expected to function in heterologous gene expression in similar ways.

Those cells having existing homologous regulator systems may be used in the present invention for the expression of heterologous DNA simply by the insertion of the DNA to be expressed in the appropriate position in the genome and in the correct orientation for expression. Thus a *Salmonella* or *Shigella* strain, as described above, may be used in this fashion. Host cells suitable for use in the present invention will include but are not limited to *Escherichia, Salmonella, Bacillus, Acinetobacter, Streptomyces, Methylobacter, Rhodococcus, Corynebacterium, Pseudomonas, Rhodobacter*, and *Synechocystis*.

Particularly suitable in the present invention are members of the enteric class of bacteria. Enteric bacteria are members of the family Enterobacteriaceae and include such members as *Escherichia, Salmonella*, and *Shigella*. They are gram-negative straight rods, 0.3-1.0×1.0-6.0 mm, motile by peritrichous flagella (except for *Tatumella*) or nonmotile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of *Shigella dysenteriae* 0 group 1 and *Xenorhabdus nematophilus*, catalase positive. Nitrate is reduced to nitrite (except by some strains of *Erwinia* and *Yersina*). The G+C content of DNA is 38-60 mol % ($T_m$, Bd). DNAs from species within most genera are at least 20% related to one another and to *Escherichia coli*, the type species of the family. Notable exceptions are species of *Yersina, Proteus, Providenica, Hafnia* and *Edwardsiella*, whose DNAs are 10-20% related to those of species from other genera. Except for *Erwinia chrysanthemi*, all species tested contain the enterobacterial common antigen (Bergy's Manual of Systematic Bacteriology, D. H. Bergy et al., Baltimore: Williams and Wilkins, 1984).

It is clear that host cells comprising the present regulator systems are suitable for use in the invention. However, where it is desired to find new strains having the present regulator systems, or to identify new regulator genes having greater functionality in non-native host cells, it will be possible to use the sequence information provided in the literature and in this disclosure to identify and isolate such homologs.

Isolation of Homologs

A specific yhcS regulator has been identified in the *E. coli* genome and has the nucleic acid sequence as set forth in SEQ ID NO:1. The promoter region of the yhcRQP operon, responsive to the expression of this yhcS regulator has the nucleic acid sequence as set forth in SEQ ID NO:3. It will be apparent to the skilled artisan that homologs to the *E. coli* sequences or others cited in the literature may easily be identified based on current practices in molecular biology, and such homologs will be equally applicable and useful in the present invention. For example, one of skill in the art may use the nucleic acid molecules of the instant invention to isolate cDNAs and genes encoding a homologous YhcS protein from the same or other bacterium species. Isolation of homologous genes using sequence-dependent protocols is well known in the art.

Examples of sequence-dependent protocols include, but are not limited to, methods of nucleic acid hybridization, and methods of DNA and RNA amplification as exemplified by various uses of nucleic acid amplification technologies (e.g., PCR or ligase chain reaction).

For example, yhcS gene, either as cDNA or genomic DNA, could be isolated directly by using all or a portion of the instant nucleic acid molecule as DNA hybridization probes to screen libraries from any desired bacterium employing methodology well known to those skilled in the art. Specific oligonucleotide probes based upon the instant yhcS gene sequence can be designed and synthesized by methods known in the art (Sambrook supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid molecule may be used in polymerase chain reaction protocols to amplify longer nucleic acid molecules encoding homologous yhcS genes from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor. Alternatively, the second primer sequence may be based upon sequences derived from the cloning vector. For example, the skilled artisan can follow the RACE protocol (Frohman et al., *Proc. Natl. Acad. Sci. USA* 85:8998-9002 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Invitrogen, Carlsbad, Calif.), specific 3' or 5' cDNA fragments can be isolated (Ohara et al., *Proc. Nat. Acad. Sci. USA* 86:5673-5677 (1989); Loh et al., *Science* 243:217-220 (1989)). Products generated by the 3' and 5' RACE procedures can be combined to generate full-length cDNAs (Frohman et al., *Techniques* 1:165 (1989)).

Alternatively the yhcS sequences may be employed as an hybridization reagent for the identification of homologs. The basic components of a nucleic acid hybridization test include a probe, a sample suspected of containing the gene or gene fragment of interest, and a specific hybridization method. Probes are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151(1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Heterologous DNA Expression

Once a host cell comprising a yhcS regulator and the responsive yhcRQP operon has been identified or constructed it will be necessary to insert the heterologous nucleic acid molecule into the genome in the position that will be appropriate for expression. Methods for the transformation of microbial cells and integration of DNA into a genome are common and well known in the art (see Sambrook supra). Typically a transformation vector is constructed for this purpose containing the essential elements for transformation and DNA integration. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Heterologous nucleic acid molecules suitable for expression by the methods of the invention are virtually unlimited. In some instances the heterologous nucleic acid molecule may not encode a protein and be expressed for the purpose of controlling or suppressing (as in antisense orientation for example) other genetic elements in the genome. More commonly, the foreign DNA will encode a protein and typically an enzyme that is part of a pathway. It will be appreciated that a single DNA fragment may be expressed by the present method or several linked fragments comprising all or a part of an enzymatic pathway. It is therefore within the scope of the present invention to express heterologous nucleic acid molecules encoding at least one protein wherein the at least one protein is part of an enzymatic biosynthetic pathway producing a product selected from the group consisting of isoprenoids, terpenoids, tetrapyrroles, polyketides, vitamins, amino acids, fatty acids, proteins, nucleic acids, carbohydrates, antimicrobial agents, and anticancer agents.

In some instances it will be useful to monitor the expression or activation of the regulator systems through the use of a reporter. Reporters are common and well known in the art and a non-inclusive list of those suitable in the present invention are luxCDABE, bgaB, cat, dsRed, galK, gfp, lacZ, luc, luxAB, nptII, phoA, uidA, and xylE.

One of the key advantages of the present invention is the ability to control the expression of the heterologous DNA by the action of an inducer. Applicant's discovery that the present regulator genes are responsive to aromatic carboxylic acids is fortuitous in that these compounds are inexpensive and easily obtained. Any aromatic carboxylic acid will have utility in the present method where para-hydroxybenzoic acid, para-hydroxycinnamic acid, cinnamic acid, salicylic acid, benzoic acid, and 1-napthoic acid are preferred.

Description of the Preferred Embodiments

As described in the following examples, during the course of LuxArray and DNA array analyses, Applicants discovered that expression of an *E. coli* operon, yhcRQP, was highly induced by treatment of *E. coli* cells with aromatic carboxylic acids, such a para-hydroxybenzoic acid (pHBA), para-hydroxycinnamic acid (pHCA), and cinnamic acid (CA). A luxCDABE gene fusion with the promoter region of this operon controlling the bioluminescent reporter was used to characterize expression of this operon. In the absence of inducing molecules the expression level was very low, just slightly above background. However, when the cell was treated with inducer, the expression level was dramatically elevated, where expression increased nearly 1000-fold. This represents much higher expression than found in typical LysR family members. Furthermore, the expression level was dependent on the concentration of inducer added.

The gene immediately upstream of the yhcRQP operon at open reading frame b3243, yhcS, is a putative member of the LysR family of transcription regulators. Using a transposon insertion mutation in yhcS, expression of the yhcRQP-luxCDABE gene fusion was no longer induced by aromatic carboxylic acids. Thus, it was shown that yhcS encodes a positive-acting transcriptional regulator responsible for the dramatic, tunable changes in gene expression of the yhcRQP operon.

This promoter/regulator system can be used to control and regulate expression of other genes and operons of interest by applying standard molecular biology methods. Furthermore, by analogy to other LysR family proteins, the YhcS protein likely binds to these aromatic carboxylic acid molecules and changes conformation such that it activates gene expression upon DNA binding. This conformation change may be useful to sense small molecules in nano-scale systems.

EXAMPLES

The present invention is further defined in the following Examples, in which all parts and percentages are by weight and degrees in Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*; Cold Spring Harbor Laboratory Press: Cold Spring Harbor, N.Y. (1989); by T. J. Silhavy, M. L. Bennan, and L. W. Enquist, *Experiments with Gene Fusions*, Cold Spring Harbor Laboratory, Cold Spring Harbor, N.Y. (1984); and by Ausubel, F. M. et al., *Current Protocols in Molecular Biology*, pub. by Greene Publishing Assoc. and Wiley-Interscience, Hoboken, N.J. (1987).

Standard genetic methods for transduction used in the Examples are well known in the art and are described by Miller, J. H., *Experiments in Molecular Genetics*, Cold Spring Harbor Laboratory Press, Cold Spring Harbor, N.Y. (1972).

The meaning of abbreviations is as follows: "kb" means kilobase(s), "hr" means hour(s), "min" means minute(s), "sec" means second(s), "d" means day(s), "ml" means milliliter(s), "µl" means microliter(s), "nl" means nanoliter(s), "µg" means microgram(s), "ng" means nanogram(s), "mM" means millimolar, "µM" means micromolar, "nm" means nanometer(s), "$OD_{600}$" means the optical density measured at a wavelength of 600 nm, "RLU" means relative light units.

Media and Culture Conditions:

Materials and methods suitable for the maintenance and growth of bacterial cultures were found in *Experiments in Molecular Genetics* (Jeffrey H. Miller), Cold Spring Harbor Laboratory Press, Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210-213, American Society for Microbiology, Washington, D.C. (1981); or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), BD Diagnostic Systems (Sparks, Md.), Invitrogen Corp. (Carlsbad, Calif.), or Sigma Chemical Company (St. Louis, Mo.) unless otherwise specified.

LB medium contains the following per liter of medium: Bacto-tryptone (10 g), Bacto-yeast extract (5 g), and NaCl (10 g).

Vogel-Bonner medium contains the following per liter: 0.2 g $MgSO_4.7H_2O$, 2 g citric acid.$1H_2O$, 10 g $K_2HPO_4$ and 3.5 g $NaNH_4HPO_4.4H_2O$.

Minimal M9 medium contains the following per liter of medium: $Na_2HPO_4$ (6 g), $KH_2PO_4$ (3 g), NaCl (0.5 g), and $NH_4Cl$ (1 g).

Above media were autoclaved for sterilization then 10 ml of 0.01 M $CaCl_2$ and 1 ml of 1 M $MgSO_4.7H_2O$ were added to M9 medium. Vitamin B1 (thiamin) was added at 0.0001% to both Vogel-Bonner and M9 media. Carbon source and other nutrients and supplements were added as mentioned in the Examples. All additions were pre-sterilized before they were added to the media.

Molecular Biology Techniques:

Restriction enzyme digestions, ligations, transformations, and methods for agarose gel electrophoresis were performed as described in Sambrook supra. Polymerase Chain Reactions (PCR) techniques were found in White, B., *PCR Protocols: Current Methods and Applications*, Volume 15 (1993) Humana Press Inc, Totowa, N.J.

Example 1

Gene Expression Profiling of Para-Hydroxybenzoate-Treated *E. coli* Cells

The alterations in the *E. coli* gene expression profile upon exposure to pHBA were examined using DNA microarray technology. *E. coli* strain DE112 (Van Dyk et al. *Appl. Environ. Microbiol.* 60:1414-1420 (1994)) was grown in Vogel-Bonner minimal medium with glucose as a carbon source to an $OD_{600}$ of 0.2. At this point the culture was split in two flasks and pHBA in the acid form was added to one flask from a stock solution in ethanol to achieve a final pHBA concentration of 25 mM. The pH of the medium in the flask with pHBA was lowered by an unmeasured amount. An equivalent volume of ethanol without pHBA was added to the other flask. Approximately 58% growth inhibition resulted from the pHBA treatment under these conditions. Cells were harvested from the control and treated flasks at 30 and 60 minutes after pHBA addition. RNA isolation, array hybridization, and data analysis were done as previously described (Wei et al, *J. Bacteriol.* 183: 545-556 (2001), Smulski et al. *J. Bacteriol.* 183:3353-3364 (2001)). Among the genes that were highly induced by this treatment at the 60 minute time point were the yhcR, yhcQ, and yhcP genes (Table 1). The experiment was repeated, and again, these three genes were highly upregulated (Table 2). These three genes are predicted to be transcribed as an operon. The reproducible observed co-regulation in response to pHBA treatment is consistent with this prediction. Thus, these three genes will be referred to as the yhcRQP operon.

TABLE 1

Upregulation of genes in the yhcRQP operon after 60 minutes pHBA treatment, experiment 1

| Gene | Blattner No.* | Signal in untreated | Signal in pHBA treated | Ratio (treated/untreated) |
|---|---|---|---|---|
| yhcR | b3242 | 0.0190 | 1.37 | 72.3 |
| yhcQ | b3241 | 0.393 | 1.61 | 4.09 |
| yhcP | b3240 | 1.17 | 7.52 | 6.45 |

TABLE 2

Upregulation of genes in the yhcRQP operon after 60 minutes pHBA treatment, experiment 2

| Gene | Blattner No.* | Signal in untreated | Signal in pHBA treated | Ratio (treated/untreated) |
|---|---|---|---|---|
| yhcR | b3242 | 0.687 | 7.18 | 10.5 |
| yhcQ | b3241 | 0.270 | 6.02 | 22.3 |
| yhcP | b3240 | 0.994 | 12.0 | 12.1 |

*Blattner et al. Science 277: 1453-1462 (1997).

Example 2

LuxArray Analysis of Para-hydroxycinnamic Acid and Cinnamic Acid Treated *E. coli*

Gene expression profiles were done using LuxArray version 1.04, which has been fully described (Van Dyk et al. *J. Bacteriol.* 183:5496-5505 (2001), Gonye et al. U.S. Patent Application Publication 20030219736). This method utilizes a set of bioluminescent gene fusions to 1/3 of *E. coli* transcriptional units in a tolC⁻ host strain that is hypersensitive to many compounds, including pHCA. Sublethal concentrations of pHCA, 10 mM and 5 mM, and CA, 8 mM and 4 mM, at which stress and other responses can be detected using luxCDABE reporter gene fusions, were used. Each of these treatments yielded nearly identical expression patterns, suggesting a similar cellular response to these two aromatic compounds. A predominant feature observed in both these profiles was that one gene fusion, lux-a.pk035.c7, was the several hundred-fold upregulated. The lux-a.pk035.c7 gene fusion contains an *E. coli* chromosomal segment between nucleotides 3385829 and 3386761 according to the *E. coli* genomic sequence, which contains the promoter region of the putative yhcRQP operon and the entire yhcR gene and the 5' end of the yhcQ gene. This chromosomal segment is joined to the luxCDABE gene fusion in the parental plasmid, pDEW201 (Gonye et al. U.S. Patent Application Publication 20030219736) thus forming junction between yhcQ gene and luxC. Accordingly, this gene fusion will report on expression of the yhcQ gene and any other genes cotranscribed with it. As detailed in Example 1, it is likely that yhcR, yhcQ, and yhcP form an operon, thus this gene fusion is referred to as a yhcRQP-luxCDABE gene fusion. The strain containing this gene fusion was given the name DPD2411, and the plasmid within this strain that contains yhcRQP-luxCDABE gene fusion was called pDEW655.

Table 3 shows the bioluminescent response of this reporter gene fusion to pHCA, CA, and ethanol. As part of a larger LuxArray experiment, two independent, actively growing, cultures carrying the yhcRQP-luxCDABE gene fusion in LB medium were each split three ways at time zero. Two aliquots were treated with different concentrations of each chemical and the third aliquot was the untreated control. The normalized bioluminescent signal from each of two replicas in the LuxArray is shown for the measurements at four time points (in minutes).

The dramatic upregulation of expression in response to pHCA and CA treatments at each of the time points other than the initial, zero time point is clear. In contrast, ethanol treatment does not induce increased bioluminescence.

TABLE 3

Responses of the yhcRQP-luxCDABE gene fusion to pHCA, CA, or ethanol

| Treatment | Replica 1 normalized RLU | | | | Replica 2 normalized RLU | | | |
|---|---|---|---|---|---|---|---|---|
| | 0 min | 45 min | 90 min | 135 min | 0 min | 45 min | 90 min | 135 min |
| 0 mM pHCA | 0.061 | 0.071 | 0.067 | 0.039 | 0.043 | 0.04 | 0.039 | 0.022 |
| 5 mM pHCA | 0.056 | 10.695 | 14.276 | 13.533 | 0.043 | 9.325 | 14.754 | 10.587 |
| 10 mM pHCA | 0.056 | 9.094 | 14.314 | 15.283 | 0.034 | 7.31 | 11.164 | 12.867 |
| 0 mM CA | 0.03 | 0.034 | 0.024 | 0.013 | 0.08 | 0.052 | 0.032 | 0.015 |
| 4 mM CA | 0.026 | 4.092 | 5.845 | 5.394 | 0.062 | 2.928 | 4.951 | 3.678 |
| 8 mM CA | 0.022 | 4.937 | 8.379 | 6.981 | 0.054 | 3.405 | 6.193 | 5.746 |
| 0% ethanol | 0.021 | 0.023 | 0.017 | 0.009 | 0.045 | 0.028 | 0.018 | 0.008 |
| 3% ethanol | 0.024 | 0.024 | 0.022 | 0.012 | 0.038 | 0.029 | 0.026 | 0.014 |
| 5% ethanol | 0.022 | 0.014 | 0.022 | 0.015 | 0.037 | 0.017 | 0.017 | 0.014 |

Example 3

Regulation of yhcRQP Expression by YhcS

The yhcS gene of *E. coli* encodes an uncharacterized member of the LysR family of positive acting regulatory molecules. This gene is located immediately adjacent to the yhcRQP operon that was found to be upregulated by pHBA treatment in DNA array experiments and by pHCA and CA treatments in LuxArray experiments. The possibility that YhcS controls expression of yhcRQP was tested using a yhcS null mutation.

Such a mutation was found in an *E. coli* library of transposon insertion mutations constructed using the transposome system based on the Tn5 transposon (Epicentre, Madison, Wis.). A transposome is a protein-DNA complex composed of the EZ::TN<Kan-1> transposon and the EZ::TN transposase. The EZ::TN transposase is bound to the ends of the transposon, which facilitates the formation of a stable synaptic complex. The transposome requires $Mg^{+2}$ to initiate the insertion of the EZ::TN<Kan-1> transposon into target DNA. The cellular levels of $Mg^{+2}$ are sufficient to activate the transposome. Thus, the electroporation of the transposome into cells permits the in vivo insertion of the EZ::TN<Kan-1> transposon into bacterial genomes.

The EZ::TN<Kan-1> transposome was electroporated into electroporation competent *E. coli* strain DH5αE cells (Invitrogen, Carlsbad, Calif.). Following electroporation, the cells were grown in SOC medium (Initrogen) for one hour at 37° C. with aeration. Subsequently, the cells were plated onto LB agar plates containing kanamycin (50 µg/ml) (LB+Kan) and incubated overnight at 37° C. Individual colonies were inoculated into 96-well microtiter plates containing 150 µl of LB+Kan and incubated overnight at 37° C.

"Single Primer PCR" was used to determine the identity of each *E. coli* transposon mutation. Using a single DNA primer that was complementary to one end of the EZ::TN<Kan-1> transposon, PCR products were generated. Subsequently, a second DNA primer (located internal and adjacent to the PCR primer) was used to sequence the PCR products. The DNA primer used in the PCR reaction was either Kan-2FP(PCR) (SEQ ID NO:4) or Kan-2RP(PCR) (SEQ ID NO:5) and the DNA primer used for DNA sequencing was either Kan-2FP(PCR) (SEQ ID NO:4) or Kan-2RP (PCR) (SEQ ID NO:5), respectively. The PCR reaction conditions were the following: (1) 94° C., 15 minutes (2) 20 cycles –94° C., 30 seconds; 60° C., 30 seconds; 72° C., 3 minutes (3) 30 cycles –94° C., 30 seconds; 40° C., 30 seconds; 72° C., 2 minutes (4) 30 cycles –94° C., 30 seconds; 60° C., 30 seconds; 72° C., 2 minutes (5) 72° C., 7 minutes. The PCR reactions were prepared for DNA sequencing using the QIAquick PCR Purification Kit (Qiagen, Valencia, Calif.).

The yhcS transposon mutant was identified using PCR amplification primer Kan-2FP(PCR) (SEQ ID NO:4) and DNA sequencing primer Kan-2FP-1 (SEQ ID NO:6). The transposon mutation was confirmed using gene-specific primers: YhcS.F (SEQ ID NO:8) and YhcS.R (SEQ ID NO:9) and transposon-specific primers Kan-2FP-1 (SEQ ID NO:6) and Kan-2RP-1 (SEQ ID NO:7).

The size of the yhcS gene is ~929 base pairs. The transposon insertion site within the yhcS gene is ~330 base pairs away from the 5' end of yhcS. A PCR reaction done with the YhcS.F and Kan-2RP-1 primers yielded a PCR fragment ~550 base pairs and PCR primers YhcS.R and Kan-2FP-1 yielded a PCR product <400 base pairs in size.

Figure 1:
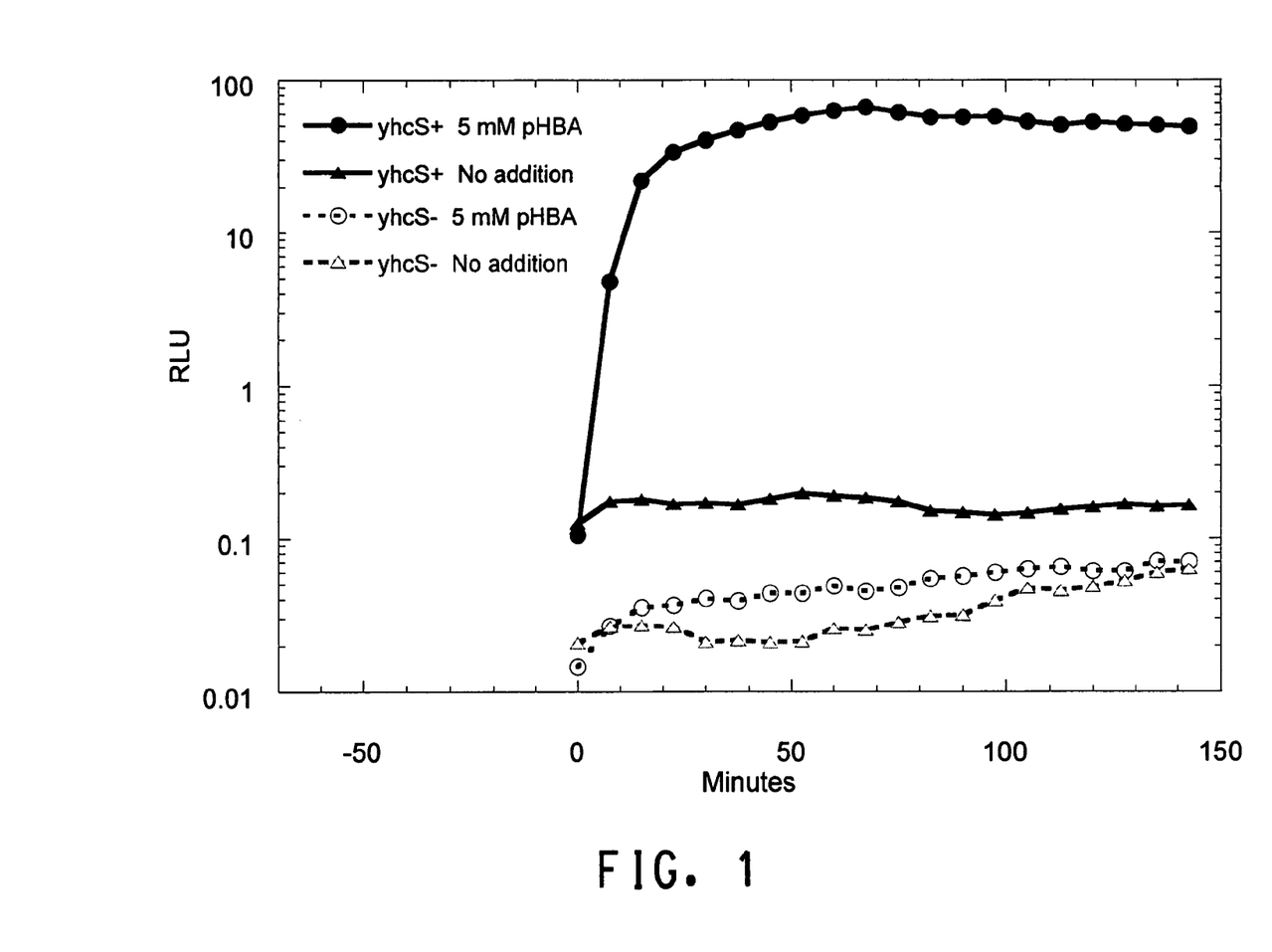
FIG. 1 shows the kinetics of the yhcRQP-luxCDABE response to pHBA in yhcS$^+$ and yhcS$^-$ host strains.

*E. coli* strain DPD2410 is the DH5αE derived strain containing the yhcS::TN<Kan> mutation. Strains DH5αE and DPD2410 were transformed with pDEW655 to generate *E. coli* strains DPD2413 and DPD2415, respectively. A single colony of each of these two strains from an LB plate containing 150 µg/ml Ampicillin was used to inoculate 200 µl LB medium in wells of a 96 well, white microplate (Microlite, Dynex Technologies, Chantilly, Va.). The plate was incubated for 90 minutes at 37° C.; then 50 µl of the cultures was added to 50 µl of LB medium or to 50 µl of LB medium containing pHBA in the acid form, which had been added from a stock solution in ethanol. The final concentration of pHBA was 5 mM and the final concentration of ethanol was 0.25%. The pH of the medium with pHBA was lowered by an unmeasured amount. The bioluminescence was quantitated with a Luminoskan Ascent microplate luminometer (Thermo Labsystems, Franklin, Mass.). The results of this study are presented in FIG. 1, which is a plot of the bioluminescence intensity in relative light units (RLU) versus time in minutes. In the Figure, addition of pHBA was made at time zero. Solid lines are the response in the yhcS+ strain, DPD2413. Dotted lines are the response in the yhcS− strain, DPD2415. Circles represent pHBA treated cultures and triangles represent untreated cultures. FIG. 1 clearly shows that pHBA induced rapid and dramatic upregulation of the yhcRQP-luxCDABE expression in the yhcS host strain, but that this upregulation was essentially abolished in the yhcS::TN<Kan> host strain.

A derivative of *E. coli* strain MG1655 (obtained from Prof. Douglas Berg, Washington University School of Medicine, St. Louis, Mich.) with the yhcS::TN<Kan> mutation was made by P1clr100Cm mediated transduction using phage grown on strain DPD2410 as a donor and selection for kanamycin resistance. The presence of the yhcS::TN<Kan> mutation in one of the resultant transductants, named DPD2433, was confirmed by PCR amplification. Plasmid pDEW655 was moved to E. coli strains MG1655 and DPD2433 by transformation, selecting for Ampicillin resistance to generate strains DPD2436 and DPD2437, respectively. The bioluminescent response of these two strains to pHBA was tested. Aliquots (50 μl) of actively growing cultures at 37° C. in LB medium that had been previously diluted, and from overnight cultures in LB medium with 150 μg/ml Ampicillin were added to 50 μl of LB medium at pH 7.0 containing pHBA as the sodium salt form. Several concentrations of pHBA were tested. Table 4 below shows the response in these two host strains at thirty minutes after cells were added to pHBA containing medium.

TABLE 4

Bioluminescence response of the yhcRQP-luxCDABE gene fusion

| [pHBA], | RLU | | Ratio treated/control | |
|---|---|---|---|---|
| mM | yhcS+ | yhcS− | yhcS+ | yhcS− |
| 100 | 0.437 | 0.045 | 0.693 | 0.055 |
| 50 | 91.7 | 0.614 | 145 | 0.753 |
| 25 | 66.6 | 1.59 | 106 | 1.95 |
| 12.5 | 30.8 | 1.82 | 48.8 | 2.23 |
| 6.2 | 16.2 | 1.42 | 25.7 | 1.75 |
| 3.1 | 10.2 | 1.16 | 16.2 | 1.42 |
| 1.6 | 6.72 | 1.02 | 10.6 | 1.25 |
| 0 | 0.631 | 0.815 | 1 | 1 |

The yhcS::TN<Kan> mutation almost completely eliminated the upregulation of expression induced by pHBA treatment at all concentrations tested. Also note that in the yhcS+ strain, the level of gene expression as quantitated by the degree of bioluminescence varied with the concentration of pHBA added. Thus, the amount of inducer added can be used to tune the expression level from this promoter.

Overall, in two different E. coli host strains, a functional YhcS was required for upregulation of yhcRQP expression in response to pHBA addition. These results prove that YhcS is a positive acting factor for upregulation of transcription of the yhcRQP operon.

Example 4

Structure Activity Relationships for YhcS Activation

Further characterization of the signals that trigger activation of YhcS, was done using the yhcRQP-luxCDABE gene fusion containing E. coli strains DPD2411 or DPD2436. Table 5 shows the results of bioluminescence activation tests done with cells in LB medium at pH 7.0, as described in Example 3. Several weak, aromatic acid molecules in addition to those shown in the Examples above activated expression. Thus, the known inducing molecules comprise pHBA, pHCA, CA, salicylate, benzoate, and 1-napthoate.

TABLE 5

Upregulation of yhcRQP-luxCDABE expression by aromatic carboxylic acids

| Experiment code* | E. coli strain | Compound | Concentration of maximum response | treated RLU | control RLU | Ratio |
|---|---|---|---|---|---|---|
| A | DPD2411 | 1-napthoate | 2.5 mM | 29.662 | 0.2244 | 132 |
| A | DPD2411 | Sodium pHBA | 25 mM | 69.678 | 0.231 | 302 |
| B | DPD2436 | Sodium benzoate | 6.2 mM | 3.759 | 0.2898 | 13 |
| C | DPD2436 | Sodium benzoate | 12.5 mM | 8.093 | 0.6792 | 12 |
| C | DPD2436 | Sodium pHBA | 50 mM | 91.658 | 0.6311 | 145 |
| D | DPD2436 | Sodium salicylate | 6.2 mM | 14.703 | 0.1908 | 77 |
| D | DPD2436 | Sodium pHBA | 50 mM | 48.643 | 0.196 | 248 |

*Experiments with the same code letter were done simultaneously using one split E. coli culture.

Compounds tested that did not induce expression were defined as those for which there resulted less than 3-fold increase in light production from E. coli strains containing pDEW655. Compounds unrelated in structure to the known inducing molecules did not induce expression. Those tested were acetate, propionate, ethanol, limonene, NaCl, polymyxin sulfate, benzalkonium chloride, gramicidin S, and SDS. In addition, several compounds related in structure to the inducing molecules were not inducers, including methyl paraben, p-hydroxystryrene, 2-biphenylcarboxylate, and L-tyrosine. Thus, the requirement for the carboxylate moiety was demonstrated by the lack of response to methyl paraben, the methyl ester of pHBA, and to p-hydroxystryrene, a molecule related to pHCA but lacking the carboxylate group. The requirement for an aromatic ring was demonstrated by the lack of response to non-aromatic carboxylic acids, acetate and propionate.

The response of this regulatory system is specific for certain aromatic carboxylic acids. This class of molecules includes compounds that are environmentally friendly and relatively inexpensive, such as sodium benzoate.

Example 5

Internal Acidification is not the Signal that Activates YhcS

All characterized activators of YhcS are weak acids such as pHBA and pHCA. Thus, the inducing condition could potentially be either acidification of the cytoplasm or presence of the conjugate molecule. The fact that non-aromatic weak acids propionate and acetate, which are known to cause cytoplasmic acidification, did not induce expression of the yhcRQP-luxCDABE gene fusion suggested that cytoplasmic acidification was not the inducing signal. This conclusion was confirmed by experiments comparing upregulation of yhcRQP-luxCDABE mediated by YhcS to that mediated by other well-known acidification responsive regulatory circuits. Three E. coli strains, each in the same host strain but carrying different, plasmid-borne, promoter-luxCDABE fusions were used. Strain DPD2411 contains a yhcRQP-luxCDABE gene fusion as described in Example 2. Strain DPD2084 contains a yciG-luxCDABE gene fusion that has been previously described. Strain DPD3282 contains a lysU-luxCDABE gene fusion that was part of the LuxA collection of gene fusions, described in Example 2. The plasmid in this strain, pDEW558, contains an *E. coli* chromosomal segment between nucleotides 4350990 and 4353107 according to the *E. coli* genomic sequence; the orientation of the chromosomal segment is such that the lysU promoter region controls expression of luxCDABE. Each of these three strains was grown overnight in Vogel-Bonner minimal medium with 0.4% glucose as the carbon source and supplemented with L-proline, L-lysine, uracil and 25 µg/ml Ampicillin. The overnight cultures were diluted into the same medium except lacking Ampicillin and incubated at 37° C. until in mid-exponential growth. Aliquots (50 µl) of these actively growing cultures were added to 50 µl of the same medium at pH 7.0 without Ampicillin but containing various concentrations of sodium acetate or sodium salicylate in the wells of a 96 well, white microplate (Microlite, Dynex Technologies). Immediately after adding the cell culture, the bioluminescence was quantitated in a microplate luminometer in the kinetic mode. Table 6 shows the results at 100 minutes after acetate addition or salicylate addition. Treatment of *E. coli* with acetate did not activate expression of yhcRQP-luxCDABE, but did activate the other two acid responsive regulatory circuits. Conversely, addition of sodium salicylate upregulated expression of yhcRQP-luxCDABE, but did not increase expression of the other two acid responsive gene fusions at the concentrations tested. Thus, it can be concluded that YhcS is not responding to acidification signals, but rather is responding to the presence of the aromatic molecules.

TABLE 6

Comparison of acid inducible gene fusions and yhcRQP-luxCDABE responses to acetate and salicylate

| Gene fusion | RLU at 100 minutes | | | | | |
|---|---|---|---|---|---|---|
| | 0 mM acetate | 80 mM acetate | 160 mM acetate | 0 mM salicylate | 0.6 mM salicylate | 5.0 mM salicylate |
| yhcRQP-luxCDABE | 0.13 | 0.14 | 0.08 | 0.32 | 7.9 | 26.0 |
| yciG-luxCDABE | 0.19 | 0.35 | 0.80 | 0.18 | 0.19 | 0.13 |
| lysU-luxCDABE | 1.3 | 1.4 | 6.0 | 1.3 | 1.3 | 0.89 |

I claim:

1. A host cell comprising:
   a) a yhcS regulator gene responsive to an aromatic carboxylic acid inducer having:
      i) an isolated nucleic acid molecule comprising nucleic acid sequence SEQ ID NO: 1;
   b) a promoter region, responsive to expression of the yhcS regulator gene having:
      i) an isolated nucleic acid molecule comprising nucleic acid sequence SEQ ID NO:3; and
   c) at least one heterologous nucleic acid molecule;
   wherein the at least one heterologous nucleic acid molecule is operably linked to the promoter region.

2. The host cell of claim 1 wherein the host cell is an enteric bacteria.

3. The host cell of claim 1 wherein the at least one heterologous nucleic acid molecule encodes at least one protein.

4. The host cell of claim 1 wherein the at least one heterologous nucleic acid encodes a reporter.

5. The host cell of claim 4 wherein the reporter is selected from the group consisting of luxCDABE, bgaB, cat, dsRed, galK, gfp, lacZ, luc, luxAB, nptll, phoA, uidA, and xylE.

6. The host cell of claim 3 wherein the at least one protein is part of an enzymatic biosynthetic pathway producing a product selected from the group consisting of isoprenoids, terpenoids, tetrapyrroles, polyketides, vitamins, amino acids, fatty acids, proteins, nucleic acids, carbohydrates, antimicrobial agents, and anticancer agents.

* * * * *

SEQUENCE LISTING

```
<160> NUMBER OF SEQ ID NOS: 9

<210> SEQ ID NO 1
<211> LENGTH: 930
<212> TYPE: DNA
<213> ORGANISM: Escherichia coli
<220> FEATURE:
<221> NAME/KEY: CDS
<222> LOCATION: (1)..(930)

<400> SEQUENCE: 1 atg gaa cga cta aaa cgc atg tcg gtg ttt gcc aaa gta gtt gaa ttt      48
Met Glu Arg Leu Lys Arg Met Ser Val Phe Ala Lys Val Val Glu Phe
1               5                  10                  15 ggc tct ttt acc gcc gcc gcc aga cag cta cag atg agc gtt tcg tcc      96
Gly Ser Phe Thr Ala Ala Ala Arg Gln Leu Gln Met Ser Val Ser Ser
                20                  25                  30 atc agt cag acg gta tca aaa ctg gaa gat gag ttg cag gta aag ctg     144
Ile Ser Gln Thr Val Ser Lys Leu Glu Asp Glu Leu Gln Val Lys Leu
            35                  40                  45 tta aac cgt agc aca cgc agc att ggc ctg acc gaa gcc ggt aga att     192
Leu Asn Arg Ser Thr Arg Ser Ile Gly Leu Thr Glu Ala Gly Arg Ile
        50                  55                  60 tac tac cag ggc tgc cgt cgt atg ctt cat gaa gtg cag gat gtt cat     240
Tyr Tyr Gln Gly Cys Arg Arg Met Leu His Glu Val Gln Asp Val His
65                  70                  75                  80 gag caa ctg tat gcc ttc aat aac acc ccc atc ggg acg cta cgc att     288
Glu Gln Leu Tyr Ala Phe Asn Asn Thr Pro Ile Gly Thr Leu Arg Ile
                85                  90                  95 ggc tgt tct tca act atg gca caa aat gtt ctc gcc ggg ctg aca gcc     336
Gly Cys Ser Ser Thr Met Ala Gln Asn Val Leu Ala Gly Leu Thr Ala
            100                 105                 110 aaa atg ctg aaa gaa tac cca ggt ttg agc gtc aat ctg gtt acc gga     384
```

```
                                                                                              -continued Lys Met Leu Lys Glu Tyr Pro Gly Leu Ser Val Asn Leu Val Thr Gly
        115                 120                 125 att cca gcc ccc gac ctg att gcc gac ggt ctg gat gtg gtg atc cgc          432
Ile Pro Ala Pro Asp Leu Ile Ala Asp Gly Leu Asp Val Val Ile Arg
130                 135                 140 gtc ggc gcg ttg cag gat tcc agc ctg ttt tcc cgc cgt ctg ggc gcg          480
Val Gly Ala Leu Gln Asp Ser Ser Leu Phe Ser Arg Arg Leu Gly Ala
145                 150                 155                 160 atg cca atg gtg gtg tgc gcc gcg aaa agc tat ctc aca caa tac ggc          528
Met Pro Met Val Val Cys Ala Ala Lys Ser Tyr Leu Thr Gln Tyr Gly
                165                 170                 175 ata ccg gaa aaa ccc gcc gat ttg agt agt cat tca tgg ctt gaa tac          576
Ile Pro Glu Lys Pro Ala Asp Leu Ser Ser His Ser Trp Leu Glu Tyr
            180                 185                 190 agc gtg cgg ccc gac aat gaa ttt gaa ctg atc gca ccg gaa ggg atc          624
Ser Val Arg Pro Asp Asn Glu Phe Glu Leu Ile Ala Pro Glu Gly Ile
        195                 200                 205 tcg act cgc ctg atc cca caa gga aga ttt gtg act aat gat ccg atg          672
Ser Thr Arg Leu Ile Pro Gln Gly Arg Phe Val Thr Asn Asp Pro Met
210                 215                 220 acg ctg gtg cgc tgg ctg acg gcg ggt gcc ggg atc gcc tac gtg ccg          720
Thr Leu Val Arg Trp Leu Thr Ala Gly Ala Gly Ile Ala Tyr Val Pro
225                 230                 235                 240 ctg atg tgg gtg atc aac gag atc aat cgt ggg gag ctg gag atc ctg          768
Leu Met Trp Val Ile Asn Glu Ile Asn Arg Gly Glu Leu Glu Ile Leu
                245                 250                 255 ctg ccg cgt tac cag tca gat cca cgc ccg gtt tat gcg tta tat acc          816
Leu Pro Arg Tyr Gln Ser Asp Pro Arg Pro Val Tyr Ala Leu Tyr Thr
            260                 265                 270 gaa aaa gat aag ctg ccg ctg aag gta cag gtc gtg atc aac tcg ctg          864
Glu Lys Asp Lys Leu Pro Leu Lys Val Gln Val Val Ile Asn Ser Leu
        275                 280                 285 acg gat tat ttt gtt gag gtc ggt aaa ttg ttt cag gag atg cac ggg          912
Thr Asp Tyr Phe Val Glu Val Gly Lys Leu Phe Gln Glu Met His Gly
290                 295                 300 cgc ggg aaa gag aag taa                                                  930
Arg Gly Lys Glu Lys
305

<210> SEQ ID NO 2
<211> LENGTH: 309
<212> TYPE: PRT
<213> ORGANISM: Escherichia coli

<400> SEQUENCE: 2

Met Glu Arg Leu Lys Arg Met Ser Val Phe Ala Lys Val Val Glu Phe
1               5                   10                  15

Gly Ser Phe Thr Ala Ala Ala Arg Gln Leu Gln Met Ser Val Ser Ser
            20                  25                  30

Ile Ser Gln Thr Val Ser Lys Leu Glu Asp Glu Leu Gln Val Lys Leu
        35                  40                  45

Leu Asn Arg Ser Thr Arg Ser Ile Gly Leu Thr Glu Ala Gly Arg Ile
    50                  55                  60

Tyr Tyr Gln Gly Cys Arg Arg Met Leu His Glu Val Gln Asp Val His
65                  70                  75                  80

Glu Gln Leu Tyr Ala Phe Asn Asn Thr Pro Ile Gly Thr Leu Arg Ile
                85                  90                  95

Gly Cys Ser Ser Thr Met Ala Gln Asn Val Leu Ala Gly Leu Thr Ala
            100                 105                 110
```

-continued

Lys Met Leu Lys Glu Tyr Pro Gly Leu Ser Val Asn Leu Val Thr Gly
            115                 120                 125

Ile Pro Ala Pro Asp Leu Ile Ala Asp Gly Leu Asp Val Val Ile Arg
        130                 135                 140

Val Gly Ala Leu Gln Asp Ser Ser Leu Phe Ser Arg Arg Leu Gly Ala
145                 150                 155                 160

Met Pro Met Val Val Cys Ala Ala Lys Ser Tyr Leu Thr Gln Tyr Gly
                165                 170                 175

Ile Pro Glu Lys Pro Ala Asp Leu Ser Ser His Ser Trp Leu Glu Tyr
            180                 185                 190

Ser Val Arg Pro Asp Asn Glu Phe Glu Leu Ile Ala Pro Glu Gly Ile
        195                 200                 205

Ser Thr Arg Leu Ile Pro Gln Gly Arg Phe Val Thr Asn Asp Pro Met
    210                 215                 220

Thr Leu Val Arg Trp Leu Thr Ala Gly Ala Gly Ile Ala Tyr Val Pro
225                 230                 235                 240

Leu Met Trp Val Ile Asn Glu Ile Asn Arg Gly Glu Leu Glu Ile Leu
                245                 250                 255

Leu Pro Arg Tyr Gln Ser Asp Pro Arg Pro Val Tyr Ala Leu Tyr Thr
            260                 265                 270

Glu Lys Asp Lys Leu Pro Leu Lys Val Gln Val Ile Asn Ser Leu
        275                 280                 285

Thr Asp Tyr Phe Val Glu Val Gly Lys Leu Phe Gln Glu Met His Gly
    290                 295                 300

Arg Gly Lys Glu Lys
305

<210> SEQ ID NO 3
<211> LENGTH: 393
<212> TYPE: DNA
<213> ORGANISM: Escherichia coli

<400> SEQUENCE: 3
ttcaacctca aacgaacagt cgcgatatca aataaaacaa gcagcaatag agcgcggtgt    60
tgaacaacgc cggatgccag acaaagtcgt agatacctgt tggcacaagt acccggcgca   120
ccagccagaa aatcgccagt gataaaagca attcaaaaaa tatcggtggg aaggacagcc   180
caaacaccac gataacggga aacagactca tgttgacctt ggttgtaaag agagagcagg   240
cgttattatt ttcagcatct gtcgccgcag agaagggcat ggaaagccgg gcgagagcaa   300
cattgctgta gattgatatt taatatatta gcgtaactgt tatgctgtta tctatattat   360
gtgatctaaa tcacttttaa gtcagagtga ata                                393

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gacggcggct ttgttgaata aatc                                           24

<210> SEQ ID NO 5
<211> LENGTH: 25
<212> TYPE: DNA
<213> ORGANISM: Artificial Sequence

```
<220> FEATURE:
<223> OTHER INFORMATION: Primer

<400> SEQUENCE: 5
ttggaattta atcgcggcct cgagc                                              25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
acctacaaca aagctctcat caacc                                              25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
gcaatgtaac atcagagatt ttgag                                              25

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aacgcatgtc ggtgtttgcc                                                    20

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
cgtgcatctc ctgaacaatt taccg                                              25
```